United States Patent [19]

Russell et al.

[11] Patent Number: 4,713,558
[45] Date of Patent: Dec. 15, 1987

[54] PATIENT MONITOR FOR PROVIDING RESPIRATION AND ELECTROCARDIOGRAM SIGNALS

[75] Inventors: Donald J. Russell, Kennessaw; Michael A. Sanders, Woodstock, both of Ga.

[73] Assignee: Healthdyne, Inc., Marietta, Ga.

[21] Appl. No.: 696,510

[22] Filed: Jan. 30, 1985

Related U.S. Application Data

[60] Division of Ser. No. 396,837, Jul. 9, 1982, Pat. No. 4,506,678, which is a continuation-in-part of Ser. No. 386,187, Jun. 7, 1982, abandoned.

[51] Int. Cl.⁴ ............................................. H03K 5/153
[52] U.S. Cl. .................................... 307/264; 307/359; 328/162
[58] Field of Search ....................... 307/359, 360, 264; 328/162; 330/9; 128/696

[56] References Cited

U.S. PATENT DOCUMENTS 3,772,604 11/1973 Hogg et al. ........................ 328/162
3,895,305 7/1975 Longman, Jr. ...................... 328/162
4,119,918 10/1978 Moser ................................ 307/359
4,263,555 4/1981 Hunka ............................... 307/359
4,323,852 4/1982 Walker .............................. 328/162
4,374,362 2/1983 Sutherland et al. ................ 307/359

Primary Examiner—John Zazworsky
Attorney, Agent, or Firm—Schwartz, Jeffery, Schwaab, Mack, Blumenthal & Evans

[57] ABSTRACT

The patient monitor includes a patient unit having a probe connected to receive a carrier signal, which probe is adapted for connection to the body of a patient to be monitored. The carrier signal is passed through the patient's body and modulated in accordance with the respirations of the patient to produce a modulated carrier signal. A carrier detection circuit is connected to receive the modulated carrier signal and produce a demodulated respiration signal. An ECG circuit also receives the carrier signal and filters out ECG signals. The respiration and ECG signals are passed to an analysis unit. Both the patient unit and analysis unit contain baseline correction circuits for maintaining a predetermined baseline.

8 Claims, 1 Drawing Figure

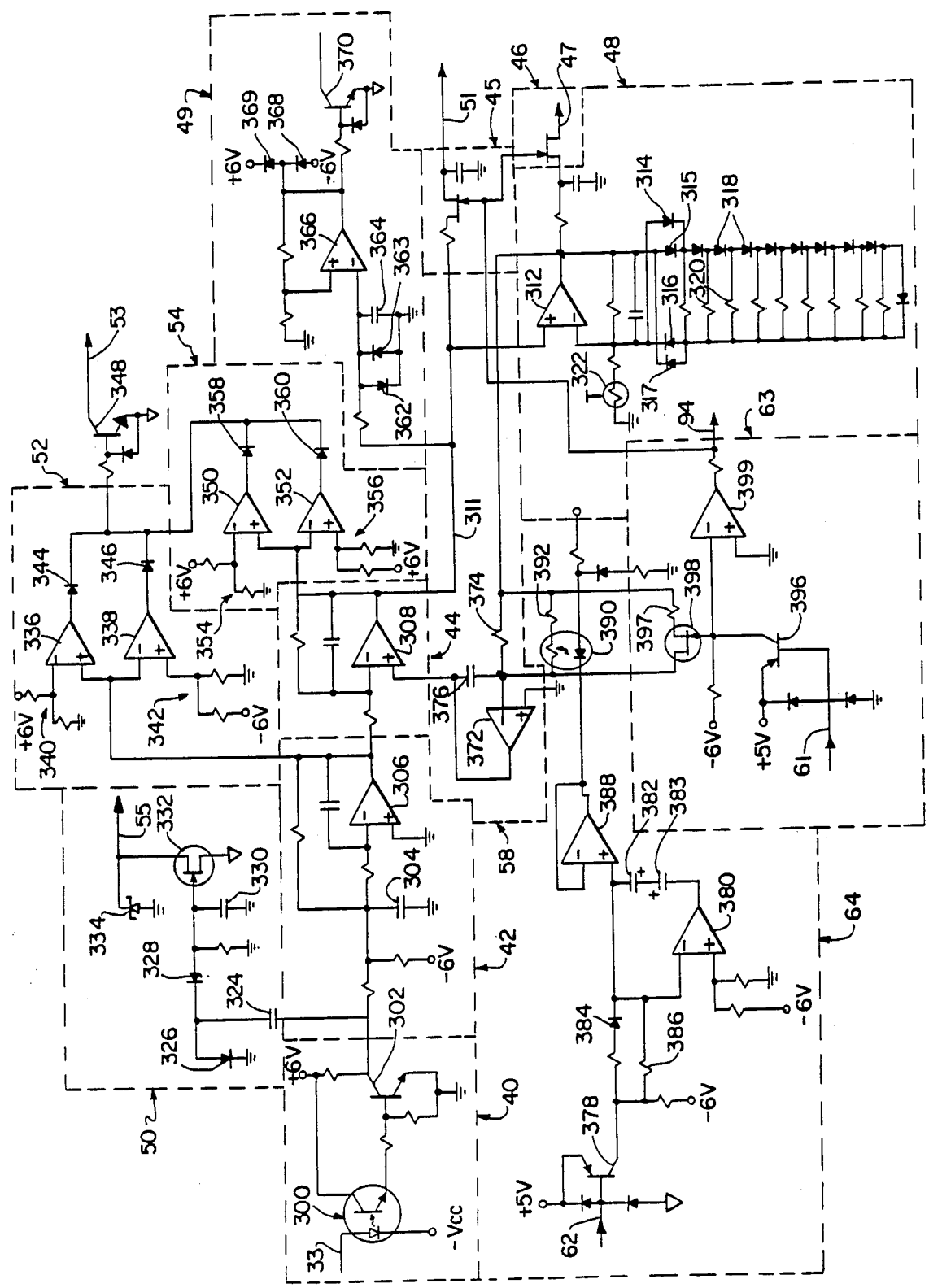

PATIENT MONITOR FOR PROVIDING RESPIRATION AND ELECTROCARDIOGRAM SIGNALS

CROSS REFERENCE TO RELATED APPLICATIONS

The present application is a divisional of U.S. application Ser. No. 396,837, filed July 9, 1982, now U.S. Pat. No. 4,506,678, which is in turn a continuation-in-part of U.S. application Ser. No. 386,187, filed June 7, 1982, now abandoned.

BACKGROUND OF THE INVENTION

1. Field of the Invention

This invention relates to systems for monitoring specific patient parameters and more particularly to systems which monitor electrocardiogram (ECG) waveforms and respiration waveforms, and which are designed to provide output signals which have a controlled amplitude and baseline.

2. Discussion of Related Art

Monitoring of specific patient parameters on a continuing basis is becoming a generally accepted diagnostic tool. This is particularly true in the case of infants which are deemed "at risk" and susceptible to sudden infant death syndrome. Such infants exhibit prolonged apnea and bradycardia episodes. Apnea is defined as the cessation of respiration, and bradycardia is defined as low heart rate A presently available monitor is a Model 16000 Infant Monitor manufactured and sold by Healthdyne, Inc., of Marietta, Ga. This infant monitor is designed to manage infants who have been determined to be at risk by providing signals indicative of the infant's respiration and heart activity. The monitor contains two control adjustments which must be made by the operator to properly set up the unit. These controls are for the sensitivity setting of the respiration and ECG channels. The monitor provides excellent operation when the sensitivity settings are proper. However, it is possible for people to poorly adjust the sensitivity settings and in so doing cause signal dropouts and accompanying false alarms. Accordingly, a need has developed for a monitor which automatically controls the sensitivity of the respiration and ECG signals.

The present invention can be used in combination with a recorder to provide a visual display of the monitored parameters. Such a recorder is disclosed in U.S. application Ser. No. 383,296, filed May 28, 1982, and in a continuation-in-part of Ser. No. 383,296, which applications are incorporated by reference herein.

SUMMARY OF THE INVENTION

One object of the present invention is to provide a patient monitor which produces respiration and ECG output signals that are indicative of the patient's respiration and heart activity, respectively.

Another object of the present invention is to provide a patient monitor which includes a patient connected unit which receives respiration and ECG signals from a patient, and a signal analysis unit which receives the respiration and ECG signals from the patient connected unit, but in which the patient connected unit and signal analysis unit are electrically isolated from each other in order to eliminate the possibility of electrical shock to the patient due to malfunctioning of the signal analysis unit.

Another object of the present invention is to provide a patient monitor having a patient connected unit and a signal analysis unit in which the patient connected unit maintains a proper baseline for received signals, and in which the signal analysis unit can control the baseline correction function of the patient connected unit.

Another object of the present invention is to provide a patient monitor which has a patient connected unit which is capable of sensing the existence of a loose lead on the patient and eliminating an output from the patient connected unit during the presence of a loose lead.

A further object of the present invention is to provide a patient monitor in which signals are transmitted from a patient connected unit to a signal analysis unit in a manner which eliminates the possibility of signal distortion due to interference by spurious signals.

Yet another object of the present invention is to provide a patient monitor having a signal analysis unit which can detect a deviation of a signal from a proper baseline at several points in the unit.

A further object of the present invention is to provide a patient monitor which includes an ECG channel in which the gain of the ECG signal is controlled automatically.

A still further object of the present invention is to provide a patient monitor having a signal analysis unit in which the baseline of a signal can be restored automatically at a controlled rate.

In accordance with the above and other objects, the patient monitor of the present invention comprises a patient unit having a probe connected to receive a carrier signal, which probe is adapted for connection to the body of a patient to be monitored, whereby the carrier signal is passed through the patient's body and modulated in accordance with respirations of the patient to produce a modulated carrier signal. A carrier detection circuit is connected to receive the modulated carrier signal and produce a demodulated respiration signal. An amplifier amplifies the demodulated respiration signal and the resultant amplified respiration signal pulse width modulate (PWM) an oscillator to produce a PWM respiration signal.

The patient monitor also includes an analysis unit which contains a carrier generation circuit for producing the carrier signal. The analysis unit also contains a pulse width demodulation circuit which receives the PWM respiration signal, demodulates the signal, and thereby produces a respiration data signal. An output circuit of the analysis unit is connected to receive the respiration data signal, amplify and level shift the respiration data signal and output the resultant respiration data signal.

The monitor also includes isolation circuitry for electrically isolating the patient unit from the analysis unit.

The patient unit also includes a baseline correction circuit for sensing the DC level of the demodulated respiration signal and adding or subtracting a DC signal to the demodulated respiration signal in response to the sensed DC level. The base line correction circuit includes a capacitor which is charged in response to the sensed DC level. The patient monitor also includes a circuit for changing the charging rate of the capacitor when the DC level of the respiration data signal reaches a predetermined amount. This charging rate circuit comprises a circuit contained in the analysis unit for deactivating the carrier generation circuit to stop the production of the carrier signal, and a circuit in the patient unit for sensing the lack of carrier signal and reducing the charging time constant of the capacitor in response thereto.

The analysis unit also includes a baseline correction circuit for sensing the DC level of the respiration data signal and adding or subtracting a DC signal to the respiration data signal in response to the sensed DC level. The analysis unit baseline correction circuit includes a capacitor which is charged in accordance with the sensed DC level and includes circuitry for varying the rate of charging of the capacitor. The circuit for varying the rate of charging the capacitor includes a circuit for reducing the charging time constant of the capacitor when the DC level of the respiration data signal is above or below predetermined limits. This rapid charge circuitry includes a programmed microprocessor, and a pair of comparator circuits connected to receive the respiration data signal and produce outputs when the respiration data signal is above or below upper and lower limits, respectively.

The patient monitor also includes an ECG sensing circuit which includes a filter contained in the patient unit for passing frequencies associated with an ECG signal. The ECG circuit also includes an amplifier for amplifying the frequencies passed by the filter to produce an amplified ECG signal, and a frequency modulation circuit connected to frequency modulate the amplified ECG signal to produce a PWM ECG signal. The amplifier and frequency modulation circuit are contained in the patient unit, and a frequency demodulation circuit is contained in the analysis unit for demodulating the PWM ECG signal to produce an ECG data signal. An ECG output circuit is contained in the analysis unit for receiving the ECG data signal, amplifying, level shifting and outputting that signal.

The ECG output circuit includes an automatic gain control circuit for controlling the amplitude of the ECG data signal to within predetermined limits. The automatic gain control circuit includes a gain controllable amplifier in the form of an operational amplifier with a variable resistance optical coupler contained in a feedback loop, and a gain control circuit in the form of an integrator circuit having an input connected to the output of the gain controllable amplifier and having an output connected to the control input of the optical coupler.

The monitor also includes an ECG baseline correction circuit in the patient unit for sensing the DC level of the amplified ECG signal and adding or subtracting a DC signal to the amplified ECG signal in response to this sensed DC level. The ECG baseline correction circuit includes a capacitor which is charged in accordance with the sensed DC level.

The charging time constant of capacitor of the ECG baseline circuit varied in a manner similar to the variation of the charging time constant of the capacitor in the respiration baseline correction circuit of the patient unit. That is, when the DC level of the respiration data signal reaches a predetermined level, the carrier generation circuit is deactivated thus stopping the generation of the carrier signal. A circuit in the patient unit senses the cessation of the carrier signal and reduces the charging time constants of the capacitors in both the ECG baseline correction circuit and the respiration baseline correction circuit. The carrier generation circuit is similarly deactivated due to a high DC level of the ECG data signal.

BRIEF DESCRIPTION OF THE DRAWING

The above and other objects of the invention will become more readily apparent when the invention is more fully described below, reference being had to the accompanying drawing in which:

The FIGURE is a schematic diagram showing the respiration channel of the signal analysis unit of the present invention.

DETAILED DESCRIPTION OF THE PREFERRED EMBODIMENT The description set forth herein is limited to the operation of the baseline correction circuit and accompanying components. The operation of the overall system is set forth in U.S. Pat. No. 4,506,678, the disclosure of which is incorporated herein by reference.

The FIGURE shows the respiration channel of the signal analysis unit of the present invention. The respiration channel is isolated from the patient unit by optical coupler 300 which receives the frequency modulated respiration signal on line 33 and optically couples this signal to transistor 302. The isolated signal from transistor 302 is passed to demodulation circuit 42 which comprises a low pass filter which includes capacitor 304, and an integrator which receives the output of the low pass filter. The integrator is formed from operational amplifier 306 and a feedback capacitor. The demodulated signal is connected to the inverting input of amplifier 308 which is biased to provide gain to the signal and pass only the frequencies of interest. A linear output from amplifier 308 is provided on line 311 to switch 45 which comprises a single FET having an output connected to line 51. The output of amplifier 308 is also provided to logarithmic conversion circuit 48. Circuit 48 includes operational amplifier 312, the output of which is fed back to its inverting input through steering diodes 314–317 and a ladder network comprising diodes 318 and resistors 320. Diodes 318 are connected in series and each has its anode connected to one terminal of a resistor 320. The opposite terminals of resistors 320 are connected together and to the anodes of diodes 316 and 317. Temperature compensation is provided by thermistor 322. As can be seen, the output of the operational amplifier 312 is fed back through the appropriate steering diodes and one or more of diodes 318 to the inverting input of the amplifier. Accordingly, the output of amplifier 312 is the logarithm of the input. As the input voltage increases, diodes 318 are incrementally included in the feedback path to increase the range of the logarithmic amplifier. The log output is provided on line 51 through switch 46, which comprises a single FET, to output line 47.

Also connected to the output of transistor 302 is the loose lead detector 50 which comprises input capacitor 324, clamping diode 326 and steering diode 328. Steering diode 328 is connected to the gate of FET 332. A capacitor 330 is also connected to that gate. The output of FET 332 is presented to the microprocessor through line 55. A zener diode 334 provides input protection for the microprocessor. Clearly, when no signal is present on line 33, the voltage to the gate of FET 332 increases and a low signal is passed along line 55 to the microprocessor.

The output of operational amplifier 306 is also passed to baseline detection circuit 52 which comprises comparators 336 and 338. The inverting input of comparator 336 is connected to a positive voltage source and the non-inverting input of comparator 338 is connected to a negative voltage source. The output of comparator 306 is connected to the non-inverting input of comparator 336 and the inverting input of comparator 338. Accordingly, if the level of the signal from comparator 306 goes above or below the level indicated by positive voltage source 340 or negative voltage source 342, respectively, a signal will be passed through diode 344 or 346, respectively, to transistor 348 to turn that transistor on and pass a signal through line 53 to the microprocessor.

Similarly, a second baseline detection circuit 54 is connected to the output of operational amplifier 308. Baseline detector 54 is identical to offset baseline detector 52 and comprises comparators 350 and 352, voltage sources 354 and 356, and diodes 358 and 360. The output of circuit 54 sends a signal to the microprocessor through transistor 348.

The output of operational amplifier 308 is also passed to signal shaping circuit 49 which comprises clamping diodes 362 and 363, capacitor 364, operational amplifier 366 and output transistor 370. The signal to shaping circuit 49 is clamped by diodes 362 and 363, averaged by capacitor 364 and fed to amplifier 366. Amplifier 366 is connected with positive feedback to produce a square wave with hysteresis each time that the respiration data signal goes above and below zero. The output of amplifier 366 is clamped to ±6 volts by diodes 369 and 368, respectively. The output is also connected to the input of transistor 370 which passes the shaped signal to the microprocessor.

The output of logarithmic amplifier 48 is fed back to the input of baseline correction circuit 58. Circuit 58 comprises resistor 374 and an integrator comprising operational amplifier 372 and capacitor 376. The output of operational amplifier 372 is connected to the non-inverting input of amplifier 308. Accordingly, it can be seen that as the average signal from logarithmic amplifier 48 deviates from zero volts, the output of amplifier 372 will fluctuate and be added to the respiration data signal in amplifier 308 to return the baseline to zero volts.

The charge on capacitor 376 can be varied more rapidly by turning on FET 398 of the fast correction circuit 63. FET 398 is effective to place a low value resistance 397 in parallel with resistor 374. Accordingly, by turning on FET 398, the charge on the integrator of the baseline correction circuit 58 will be allowed to vary more rapidly. The gate of FET 398 is connected to the output of transistor 396, the base of which is connected through line 61 to an output of the microprocessor. Accordingly, the microprocessor can turn on FET 398 by an appropriate signal on line 61. The output of transistor 396 is also passed to operational amplifier 399 which sends an output to turn off switches 45 and 46 by applying a negative signal to their gate inputs, and thus eliminate the linear respiration output on line 51 and the logarithmic output on line 47. Consequently, a display of the respiration signal will be stopped during the fast restore period.

Due to the extremely slow frequency of the respiration data signal, it may be useful to restore the baseline to the appropriate level by varying the charge on the integrator of baseline correction circuit 58 at a rate which is intermediate that provided by resistors 374 and 397. Accordingly, a medium slow charge circuit is included which comprises variable resistor optical coupler 390 which has a variable resistance in series with resistor 392. This series resistance is in parallel with resistor 374. Accordingly, when optical coupler 390 is turned on, a medium resistance is placed in parallel with high value resistance 374. Optical coupler 390 has a control input connected to the output of buffer 388. The input to buffer 388 is received from transistor 378 through diode 384. Transistor 378 is also connected through resistor 386 to the input of an integrator comprising operational amplifier 380 and capacitors 382 and 383. Clearly, the rate of charge can be varied by the microprocessor when a signal is provided on line 62 to turn on transistor 378. The signal immediately causes a variation in the resistance of optical coupler 390, thus varying the time constant of the baseline correction circuit. Also, this time constant is reduced in accordance with the amount of time the signal is maintained by the integrator comprising amplifier 380 and capacitors 382 and 383. Back-to-back polar capacitors are used in the integrator to allow the integrator to output either polarity. The integrator charging time is rapid, so that the variable time constant rapidly changes toward fast under microprocessor control. Integrator discharge time is slow so that the variable time constant slowly changes toward slow under the microprocessor control.

In operation, when a signal is received by optical coupler 300, that signal is electrically isolated from the patient unit and passed to the demodulation circuit which includes capacitor 304 and integrator 306. If no signal is received, the microprocessor is notified through FET 332 and line 55, and a loose lead alarm is actuated.

The offset level of the demodulated output is compared in comparators 336 and 338 to maximum and minimum the prescribed range, transistor 348 is actuated to notify the microprocessor.

The demodulated respiration data signal is amplified in amplifier 308. The offset of the amplifier output is again checked with permitted maximum and minimum values and, if outside the acceptable range, the microprocessor is notified by a signal from transistor 348. The ECG data signal is also directly passed to positive feedback amplifier 366 which acts as a zero crossing detector to notify the microprocessor of each respiration event through transistor 370. Further, the amplified ECG data signal is passed to switch 45 which, if fast restoration of the baseline is not being performed, passes the signal to linear respiration output lead 51. The linear output is also passed to logarithmic amplifier 48 which logarithmically amplifies the signal and passes it through switch 46 to output line 47. If a display of the signal is required, an appropriate display device can be attached to either line 47 or line 51.

If fast baseline restoration is required, a signal is produced on line 61 which turns on FET 398 to place resistor 397 in parallel with resistor 374 thus reducing the time constant of the baseline correction circuit. After fast baseline restoration is complete, medium slow variable baseline restoration is effected by a signal on line 62 which controls the resistance of optical coupler 390 which is placed in series with resistor 392 and which combination is placed in parallel with resistor 374. The medium slow variable baseline rate is controlled by the output of the integrator circuit comprising operational amplifier 380 and capacitors 382 and 383.

The foregoing description is set forth for the purpose of illustrating the invention but is not meant to limit the scope thereof in any way. Clearly numerous modifications, additions, and other changes can be made to the present invention without departing from the scope thereof as set forth in the appended claims.

We claim:

1. A baseline correction circuit, comprising:
   a line carrying a signal intended to have a predetermined DC level;
   first means for sensing said DC level and altering said DC level at a rate determined by a time constant when said DC level varies from said predetermined DC level;
   second means for detecting said DC level and producing a baseline correction signal when said DC level is outside of a predetermined range; and
   control means responsive to said baseline correction signal to alter said time constant of said first means so as to alter the rate at which said DC level is altered by said first means;
   wherein said first means comprises a charge storage device, said time constant being a time constant of said charge storage device, and said control means comprises a first circuit for altering said time constant at a predetermined rate and by controlled variable amounts.

2. A baseline correction circuit as claimed in claim 1 wherein said charge storage device comprises an integrator and said control means further comprises a second circuit for altering said time constant of said integrator by a fixed amount for a controlled time duration.

3. A baseline correction circuit as claimed in claim 2 wherein said integrator includes a variable impedance element and said first circuit comprises means for varying the impedance of said variable impedance element.

4. A baseline correction circuit as claimed in claim 3 wherein said first circuit includes a further integrator having an output connected to vary the impedance of said variable impedance element and having an input connected to receive a correction signal such that said impedance of said variable impedance element is changed by an amount determined by the time duration of said correction signal at a rate determined by a time constant of said further integrator.

5. A baselne correction circuit as claimed in claim 1 wherein said second means comprises a differential amplifier connected to receive a signal indicative of said DC level and a signal indicative of a reference level.

6. A baseline correction circuit as claimed in claim 1 wherein said charge storage means comprises an integrator and said first means further comprises a differential amplifier circuit having a feedback loop containing said integrator and having an input for receiving said signal.

7. A baseline correction circuit as claimed in claim 1 wherein said first means comprises a differential amplifier having a feedback loop and a capacitor connected in said feedback loop of said differential amplifier.

8. A baseline correction circuit for maintaining a predetermined DC level of an alternating signal, comprising:
   a line containing said alternating signal;
   a differential amplifier having one input receiving said alternating signal, having a second input and having an output;
   a charge storage circuit having an input connected to said differential amplifier output and having an output connected to said other input of said differential amplifier, said charge storage circuit having an accumulated charge level which change in response to a deviation of the DC level of the signal on said differential amplifier output from said predetermined DC level and presenting said accumulated charge to said other input of said differential amplifier for altering the DC level at said differential amplifier output, said charge storage circuit operating with a predetermined time constant;
   means for altering said time constant in response to a baseline correction signal, said altering means being effective to change said time constant from said predetermined time constant only during the presence of said baseline correction signal; and
   means for changing said time consant at a predetermined rate in response to a second baseline correction signal.

* * * * *